US009021865B1

(12) United States Patent
D'Onofrio

(10) Patent No.: US 9,021,865 B1
(45) Date of Patent: May 5, 2015

(54) APPARATUS AND METHOD FOR MEASURING PERMEATION OF CONTAMINANTS THROUGH PROTECTIVE MATERIALS

(75) Inventor: Terrence G. D'Onofrio, Bel Air, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 505 days.

(21) Appl. No.: 13/404,538

(22) Filed: Feb. 24, 2012

Related U.S. Application Data

(60) Provisional application No. 61/448,382, filed on Mar. 2, 2011.

(51) Int. Cl.
*G01N 15/08* (2006.01)
*G01N 11/08* (2006.01)

(52) U.S. Cl.
CPC ................. *G01N 11/08* (2013.01); *G01N 15/08* (2013.01)

(58) Field of Classification Search
CPC ...................................................... G01N 15/08
USPC .......... 73/37, 38, 40; 702/34, 35, 50, 140, 185
See application file for complete search history.

(56) References Cited

U.S. PATENT DOCUMENTS

| 7,306,729 | B2 * | 12/2007 | Bacino et al. ............ 210/500.22 |
| 7,594,425 | B2 * | 9/2009 | Lewnard et al. .................. 73/38 |
| 2009/0177412 | A1 * | 7/2009 | Phattaranawik et al. ....... 702/35 |
| 2011/0067485 | A1 * | 3/2011 | Grant et al. ....................... 73/38 |

* cited by examiner

*Primary Examiner* — Hezron E Williams
*Assistant Examiner* — Hoang Nguyen
(74) *Attorney, Agent, or Firm* — Ulysses John Biffoni

(57) ABSTRACT

A testing apparatus and method includes a PTFE layer; placing a sorbent pad on the PTFE layer; applying contaminants to a protective material; placing the protective material adjacent to the sorbent pad with the side having contaminants opposite the sorbent pad; applying a weight to the protective material causing the protective material to contact the sorbent pad, and determining any permeation of contaminants through said protective material causing exposure on the sorbent pad to the contaminants; and measuring a level of contamination of the sorbent pad upon exposure to any contaminants which permeated the protective material. A second PTFE layer may be placed in between the weight and the protective material. Additionally, another PTFE layer may be placed in between the protective material and the sorbent pad. The protective material may include any of air impermeable materials, air permeable materials, and semi-permeable materials.

12 Claims, 7 Drawing Sheets

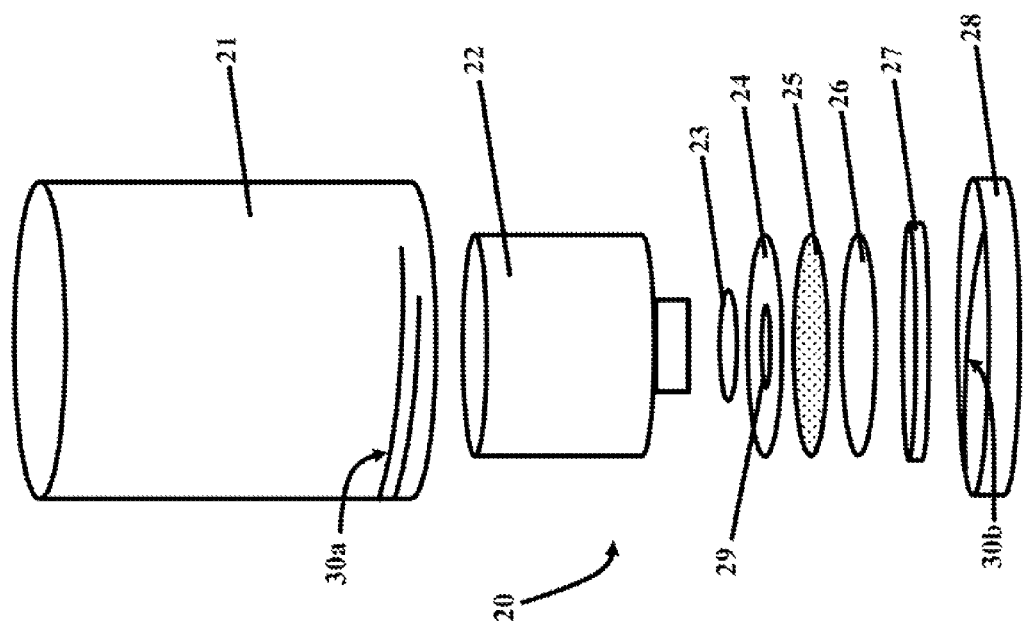

APPARATUS AND METHOD FOR MEASURING PERMEATION OF CONTAMINANTS THROUGH PROTECTIVE MATERIALS

CROSS-REFERENCE TO RELATED APPLICATION

This application claims priority to U.S. Provisional Patent Application No. 61/448,382 filed on Mar. 2, 2011, which is incorporated herein by reference in its entirety.

GOVERNMENT INTEREST

The embodiments herein may be manufactured, used, and/or licensed by or for the United States Government without the payment of royalties thereon.

BACKGROUND

1. Technical Field

The embodiments herein generally relate to quantitative permeation testing for personal protective equipment (PPE) contact scenarios including quality controls and environmental controls.

2. Description of the Related Art

Multiple methods exist for measuring permeation through protective equipment. According to the U.S. Army Test Operating Procedure (TOP), the method depends on the physical state of the contaminant, and the detection method. For liquid-contamination-vapor detection, the suggested method was the Aerosol Vapor Liquid Assessment Group (AVLAG) test cell. This apparatus uses a vapor detection scheme with an air sweep under the test swatch to gather the vapor of permeated contaminant. Detection may utilize MINICAMS® monitoring systems (available from OI Analytical, Texas, USA), sorbent tubes, or bubblers to collect the vapor. A schematic of the AVLAG cell 5, as described in the TOP, is shown in FIGS. 1A (sealed configuration) and 1B (unassembled configuration). This method permits time-resolved quantification of vapor breakthrough and environmental control. However, this method allows for the quantification of the vapor phase only, requires the use of flat swatches, and generally requires a cumbersome setup. Accordingly, this method requires a relatively significant investment in infrastructure for proper operation.

For liquid-contamination-liquid-detection, the TOP suggests using an expulsion method. A schematic of the expulsion test apparatus 10 is illustrated in FIG. 2. Here, 1 psi of pressure is applied to a contaminated swatch 14 with a 1 lb. stainless steel weight 12. Colorimetric detector paper (e.g. M8) 16 is used to determine breakthrough time. This method achieves low costs for setup and operation, time-resolved detection, application of realistic forces, and simplicity. However, this method requires bulk-liquid breakthrough for detection, and results in lack of environmental control and a lack of quantification when detector paper is used. Moreover, the TOP provides limited guidance on quantifying breakthrough using this method.

In 2007, a permeation program was initiated to examine the performance of personal protective equipment (PPE) against contaminants. Given the low volatility of the test compounds, the vapor detection method was deemed insufficient. Furthermore, the liquid-contamination-liquid-detection precludes quantification of breakthrough. Therefore, a hybrid method was devised to enable quantification of breakthrough in a contact scenario, with environmental control. This method uses a sorbent pad under the test swatch within an AVLAG cell. The swatch is contaminated in accordance with the TOP, and at a chosen time point, the swatch is removed from the cell, and the sorbent pad is extracted. The extractant is analyzed to quantify breakthrough. As part of the testing, a divinylbenzene (DVB) pad is characterized for extraction efficiency. However, this method produces a variable level of contact between the swatch and sorbent pad. This is exacerbated with non-flat swatches taken from fingers of gloves, or folded portions of protective suits. Furthermore, there is no practical method to apply relevant forces of contact. Finally, the use of the AVLAG makes this system cumbersome and each swatch is limited to a single time point.

The need for the contact scenario has been demonstrated toxicologically with rabbits during a separate study. The rabbit study used a latex swatch, known to be permeable to the nerve agent VX, as the swatch test material. The swatch was either in direct contact with the rabbit skin, or elevated by 1 cm off the skin. The elevated scenario represented a vapor only condition for exposure. The same conditions were used in both cases with regard to skin condition, contamination density, contact time, and test material. Data collected included onset of toxic signs, time-resolved acetyl cholinesterase (AChE) enzymatic activity level, and quantitation of regenerated VX in the skin and blood. All rabbits in the direct-contact scenario died, while no signs to mild signs were observed in the vapor-only rabbits. The exposure level is further supported by AChE activities. Furthermore, the level of agent measured in the skin was several orders of magnitude greater for the rabbits in the direct-contact configuration. Given that gloves and other personal protective equipment (PPE) are in direct contact with the skin, there was a need to develop additional testing techniques and systems that enables quantification in a direct contact configuration.

SUMMARY

In view of the foregoing, an embodiment herein provides an apparatus comprising a holding dish; a first polytetrafluoroethylene (PTFE) layer placed in the holding dish; a sorbent pad on the PTFE layer; a protective material having contaminants applied thereon on a side opposite said sorbent pad, wherein the protective material contacts the sorbent pad; a second PTFE layer on the protective material; a weight applied to the second PTFE layer causing the protective material to continuously contact the sorbent pad and expose the sorbent pad to the permeated contaminants; and determining measuring the level of contamination of the sorbent pad upon contact/exposure to the contaminated protective material. A third PTFE layer or a ring of colorimetric paper may be placed in between the weight and the sorbent pad. A sealed container may house the first and second PTFE layers, the housing dish, the sorbent pad, the protective material, and the weight during the exposure of the sorbent pad to the contaminated protective material. The exposure of the sorbent pad to the contaminated protective material may occur for approximately four hours or any other time period required for the test program. The protective material may comprise any of air impermeable materials, air permeable materials, and semi-permeable materials.

Another embodiment provides a method of testing comprising providing a PTFE layer; placing a sorbent pad on the PTFE layer; applying contaminants to a protective material; placing the protective material adjacent to the sorbent pad; applying a weight to the protective material causing the protective material to contact the sorbent pad, and causing the sorbent pad to become exposed to any contaminants permeating the protective material; and measuring a level of contamination of the sorbent pad upon any exposure to the contaminants permeating the protective material. The method may further comprise placing a second PTFE layer in between the weight and the protective material. Additionally, another PTFE layer may be placed in between the protective material and the sorbent pad or a ring of colorimetric paper. The method may further comprise placing the PTFE layer (including all of the PTFE layers), the sorbent pad, the protective material, and the weight in a sealed container during the exposure of the sorbent pad to the contaminated protective material. The exposure of the sorbent pad to the contaminated protective material may occur for approximately four hours, or any other time period required for the test program. The protective material may comprise any of air impermeable materials, air permeable materials, and semi-permeable materials.

Another embodiment provides a manner to test if liquid contaminant is leaking around the edge of the test swatch, which would lead to a false positive result and invalidate the testing. The characterization samples are used to indicate if the contaminant has traveled around the edge of the swatch in liquid or vapor form, and has contaminated the sorbent pad. This characterizes the system as a whole, assuming that the behavior is consistent from sample-to-sample. However, characterization samples are not capable of identifying if a sample is an outlier to the situation, and has spread the contaminant around the edge of the swatch. A liquid breach is especially likely with a seamed sample, or other swatch with extended liquid spread. Such materials have been shown to channel the liquid along the seam to the edge of the swatch. A method has been developed to identify if liquid has spread around the edge of each sample. A ring of M8 or other detector paper is used around the edge underneath the swatch. If the indicator paper turns color, the sample is invalid, as the contamination has occurred by going around the edge, as opposed to through, the material.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 3A and 3B illustrate schematic diagrams of a modified inverted expulsion test apparatus according to an embodiment herein;

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 4A:
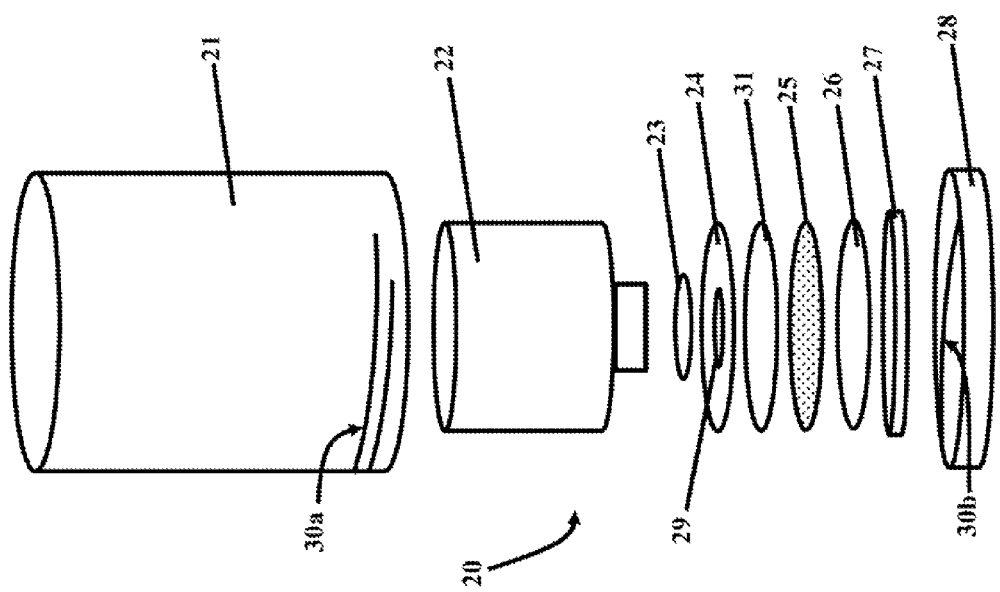
FIGS. 4A and 4B illustrate schematic diagrams of a modified inverted expulsion test apparatus according to another embodiment herein.
Figure 4B:
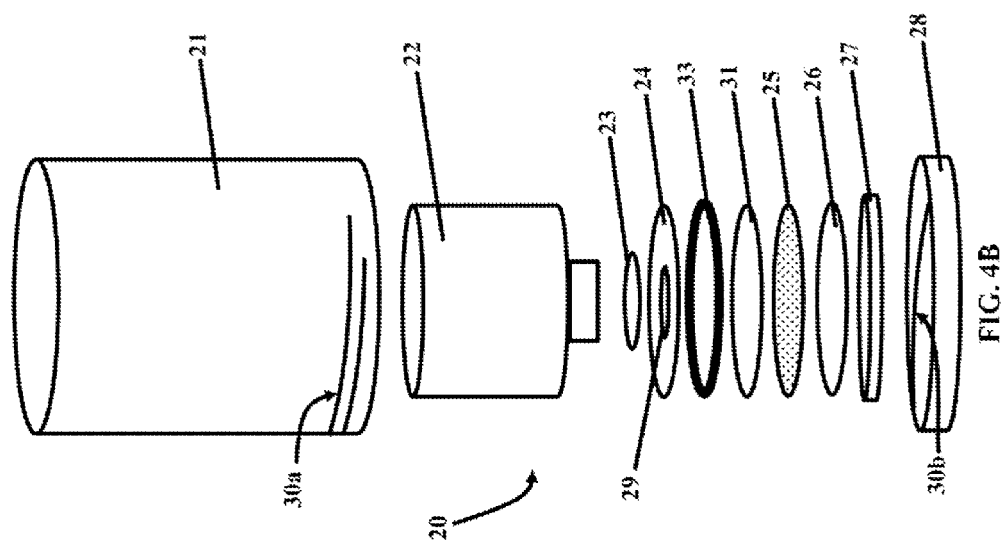
Figure 5:
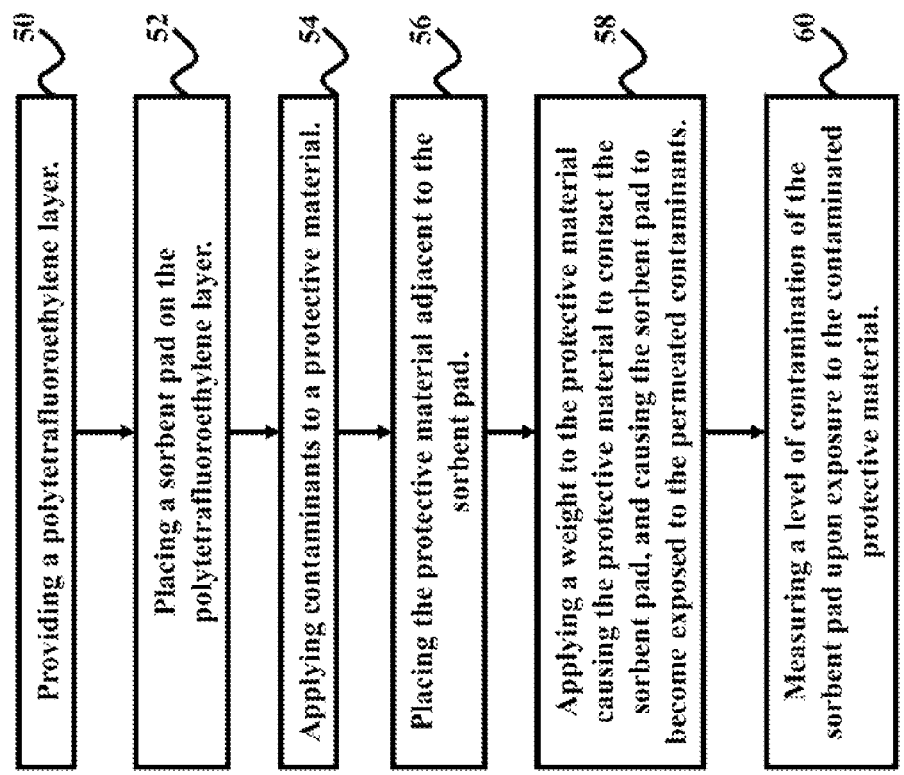
FIG. 5 is a flow diagram illustrating a preferred method according to an embodiment herein.

The embodiments herein provide a test method and apparatus to measure the permeation of contaminants through protective materials, including gloves. The test method increases the confidence of quantitative permeation test results for the contaminants, increases throughput, and reduces operational testing costs by improving controls over various quantitative measurements and environmental test conditions. The method and apparatus also evaluate glove performance under conditions that reflect more realistic use/environmental scenarios, such as mimicking forces associated with touching a contaminated surface or grasping a contaminated object. Referring now to the drawings, and more particularly to FIGS. 3 through 5, where similar reference characters denote corresponding features consistently throughout the figures, there are shown preferred embodiments.

The embodiments herein provide a test method for measuring the permeation of contaminants through materials. During experimentation, two materials were tested against one compound of interest. A single time point was chosen, which matched a previous test program. More than 75 replicates were tested for each material, as well as multiple control samples per test. The test method was based on the above-described expulsion test, detailed in the TOP for permeation testing. Improvements to the conventional test methods are achieved to enable quantification of breakthrough and temperature control. The total permeation results are summarized in Table 1 below. Samples below the quantification limit are marked "BQL". During experimentation, no permeation above the quantification limit was measured for the butyl rubber gloves. The permeated mass was measured in all latex samples.

TABLE 1

Summary of results for each material type tested

| Material | n | Average Permeation (ng) | Standard Deviation (ng) | Range (ng) |
| --- | --- | --- | --- | --- |
| Latex | 80 | 672,013 | 124,359 | 407,733–946,280 |
| Butyl | 79 | BQL | — | — |

Multiple quality control steps are incorporated into the test method to increase the confidence in the data, including a statistical design of experiments approach for test planning, chemical sample purity analysis, verification of deposited mass, sorbent pad uptake efficiency testing, logging of environmental conditions, inclusion of both positive and negative control samples, characterization samples, and analytical quality controls. Each of the quality controls are further described below.

For certain military programs, an enhancement of the hybrid method is required to satisfy the goals of high throughput, low operating costs, and a reduction in variability. The test cell is developed to combine the sorbent pad from the hybrid method with the forced mass of the expulsion test. A schematic of a test cell 20 used in accordance with the embodiments herein is shown in FIG. 3A. With the exception of the stainless steel weight 22, the cell 20 is disposable; thereby reducing the chance of cross-contamination with other equipment. During testing, environmental control is achieved using an incubator (not shown). Since vapor detection is not considered during experimental testing, the flow control hardware and infrastructure is not needed, which decreases the overall footprint, and thereby enabling expansion of the number of test cells 20. The applied forces are relevant to contacting a contaminated surface or grasping a contaminated object. The applied weight of 1 psi is mandated by the expulsion test in the TOP, and is used during industrial hygiene studies documented in peer-reviewed journals as a "heavy touch". The weight 22 also forces a constant contact between the swatch 24 and the sorbent pad 25, reducing variability in measured permeation. Although designed and tested for air impermeable materials, it is expected that this configuration is applicable to all material types, including air permeable and semi-permeable.

Another difference between the AVLAG and expulsion test methods is the contamination density. The TOP specifies the contamination level for each of these tests. For the liquid-contamination-vapor-detection scheme, the contamination is approximately 10 µL of neat contaminant, administered as approximately 1 µL droplets, evenly distributed in the 10 cm$^2$ area defined by the AVLAG cell. Thus, the contamination density for the AVLAG scheme has a nominal value of approximately 10 g/m$^2$, assuming a liquid density of approximately 1.0 g/mL.

For the liquid detection scheme, the contamination is approximately 5 µL of neat contaminant, administered as a single droplet in contaminated region 29, in the center of the swatch 24. The area is defined to be approximately 1.0 in$^2$ by the contact region of the stainless-steel weight 22. Thus, the contamination density is approximately 7.75 g/m$^2$, assuming a liquid density of approximately 1.0 g/mL. Although the contamination densities are different between the two methods, they do not differ in practical terms. Both are at an extremely high contamination density. Also, the coverage of the liquid-contamination-vapor-detection scheme is less than 10% of the surface area. Additionally, a range of contamination levels may be administered, dependent on the test requirements. This method has been tested with up to 10 µL of neat contaminant deposition.

Multiple quality control steps are incorporated into the testing to increase the confidence in the data, including a statistical design of experiments approach for test planning purity analysis, verification of deposited mass, logging of environmental conditions, positive control samples, negative controls samples, characterizations samples, sorbent pad uptake efficiency testing edge detection, and analytical quality control.

As part of the characterization of the system, the uptake efficiency of the DVB sorbent pad 25 is quantified. The purpose is to document the efficiency of the pad 25 to collect an analyte present on a contaminated surface of the swatch 24. The mass/weight of the contaminant 29 deposited is approximately 5 µg deposited as approximately 100 µL of 0.05 mg/mL solution of contaminant. This covers a larger area of the substrate swatch 24 to be contaminated which tests a larger portion of the pad 25. This better matches the breakthrough that would be expected through a swatch 24. The total mass/weight 29 deposited also fits within the calibration curve of the analytical instrumentation (not shown), and is within the range of concentrations in which the sorbent pad 25 is expected to perform.

Several additional steps are used for the uptake efficiency test. A polytetrafluoroethylene (PTFE) material disk 26 (e.g., Teflon® material available from DuPont Inc., Delaware, USA) of 2" diameter is spiked with approximately 100 µL of 0.01 mg/mL solution of contaminant in solvent and placed on a biological-chemical cell culture dish 27 (e.g., Petri dish). Once the solvent has evaporated, the disk 26 is covered with a previously prepared DVB sorbent pad 25. A second PTFE material disk 23 is used as a spacer between the pad 25 and the 1.0 pound weight 22. The entire cell 20 is sealed in a glass jar 21 with a screw cap lid 28 (using a threaded seal 30a, 30b) and incubated at approximately 37.1° C. for approximately 4 hours, or whatever time is required for the test program. After the contact time, the DVB sorbent pad 25 and disk 26 are extracted together in approximately 20 mL of acetone for approximately 30 minutes. The original contaminated disk 26 is extracted in approximately 20 mL of acetone in a separate jar (not shown). Other solvents may be used, as appropriate for the particular contaminants and/or analytical test platform. In addition, other temperatures may be used, as required for the test program.

The sorbent pads 25 or disks 26 that are extracted in approximately 20 mL acetone for approximately 30 min are analyzed with gas-chromatography-flame-photometric-detection (GC-FPD) tools (not shown), and have a quantification limit of approximately 10 ng/mL, or 200 ng total permeated mass. Improved limits of detection may be achieved with liquid-chromatography-triple-quadrupole-mass-spectrometry.

The swatches 24 are cut with an approximately 1 and $^{15}/_{16}$ inch steel ruled die and press. For the butyl gloves, an equal number of swatches 24 are taken from the palm, middle finger, thumb, and back of the hand. The samples are randomized as part of the experimental design. For latex, the swatches 24 are cut from a bulk roll of latex sheeting. The sorbent pads 25 may be 3M Empore® solid phase extraction disks, styrenedivinylbenzene, part SDB-XC (available from 3M Inc., Minnesota, USA). Gas-tight syringes can be used for agent deposition, with an approximately 250 µL syringe for the uptake efficiency experiment and an approximately 50 µL syringe for the sample testing. A calibration balance can be used to confirm deposition tool operation. Preferably, the solvents used are of chromatographic grade or better.

The small disk 23 is also used to help contain and isolate the liquid contamination. However, disk 23 does not seal the contaminated swatch region 29 from the sorbent pad 25. The possibility exists that contamination could travel around the edge of the swatch 24, and onto the sorbent pad 25, leading to a false positive or higher level of contamination.

Figure 1:
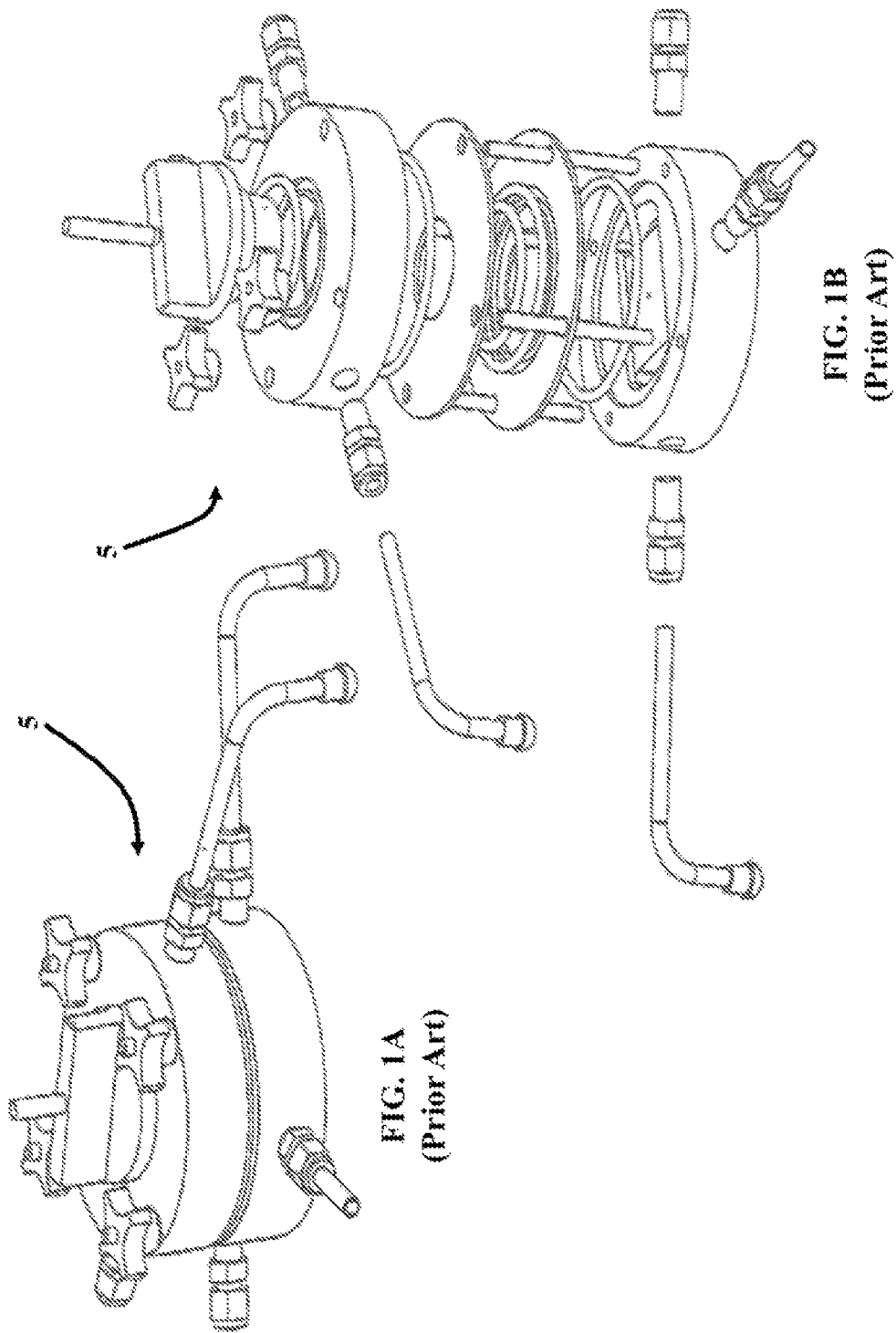
FIG. 1A illustrates a schematic diagram of a conventional AVLAG test cell in a sealed configuration.
FIG. 1B illustrates a schematic diagram of a conventional AVLAG test cell in an unassembled configuration.
Figure 2:
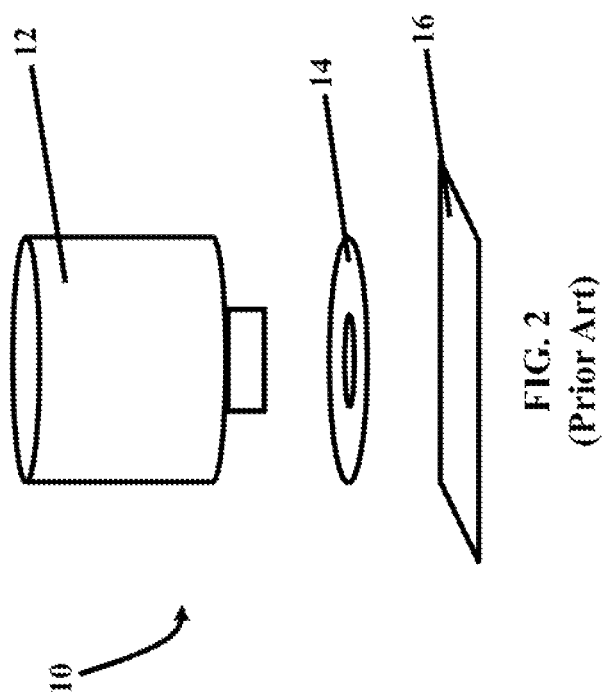
FIG. 2 illustrates a schematic diagram of a conventional expulsion test apparatus.
Figure 3B:
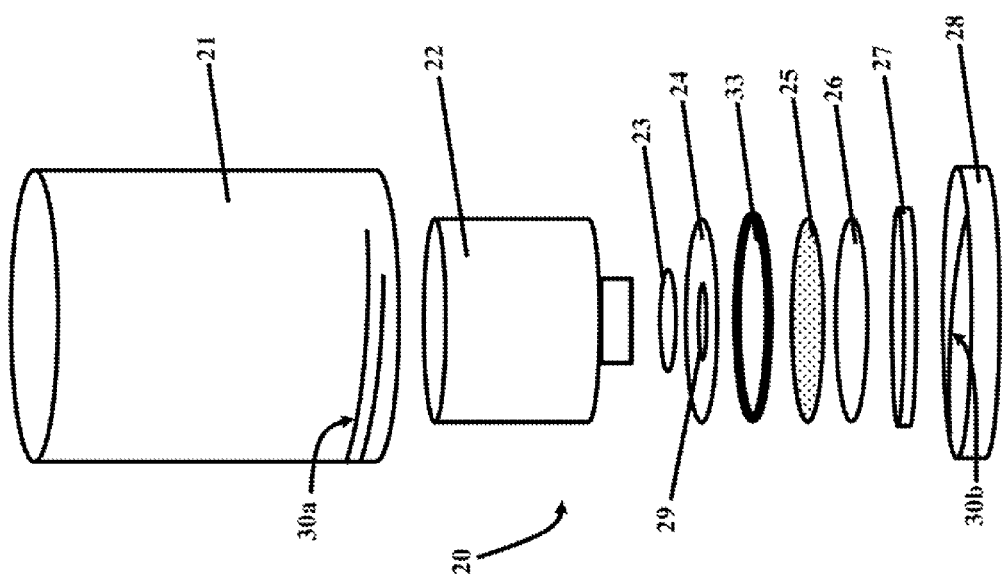

This factor can be mitigated by the use of characterization samples. Characterization samples use a contaminant impermeable barrier between the swatch 24 and the sorbent pad 25 preventing permeation through the swatch 24 from sorbing into the pad 25. For characterization samples, any contamination identified on the sorbent pad 25 most likely results from contaminants moving around the edges of the swatch 24. Contaminants measured on the characterization samples could be treated as background levels of contamination for the contaminants of interest or swatches that have not yet been tested with the test method. As backgrounds, these levels may be subtracted from the mass measured in the test samples. Alternatively, the limit of detection may be increased above the levels measured in the characterization samples. If needed, steps may be taken in future tests to better isolate the contaminated region of the swatch 24 from the pad 25, or a ring of colorimetric paper 33 may be used to indicate an invalid sample (as shown in FIG. 3B).

Additional quality control steps can be incorporated into the method to increase the confidence in the data, including purity analysis, verification of deposited mass, sorbent pad uptake efficiency testing, logging of environmental conditions, positive control samples, negative control samples, characterization samples, and analytical quality control.

Purity analysis documents the purity of the compound via an independent method. The use of a low purity contaminant may lead to inaccurate results as to the performance of the material and prevents data comparison between tests. The purity of the compound can be analyzed after the testing is complete. The repeatability of the gas-tight syringes used as a dosing tool can be measured gravimetrically for each test compound to document the performance of the tool and operator. The target mass can be deposited into a vial and the mass recorded with replicates for each compound.

The uptake potential varies as a function of contaminant, pad characteristics and substrate due to the competitive nature of contaminant interaction between the two materials. Obtaining an accurate measurement of contaminant on the surface is a difficult challenge, as many substrates are sorptive. The measurement is confounded by the sorption of the contaminant into the substrate, where it is no longer accessible by the pad 25. The contact efficiency may also be affected by the contact area of the pad 25, contact times, pressures, and contamination levels. The experimental test method only considers contaminant on disk 26 as a non-sorptive, non-reacting substrate. A single contamination level, time point, and pressure can be tested. The contamination level should be chosen to be within the calibration curve of the analytical instrumentation, and is expected to be measured within an actual permeation test. The uptake percentage can be calculated as the mass of contaminant in the pad 25 divided by the total measured contaminant on the pad 25 and disk 26. The quantification limit value, e.g. (200 ng), is used for the values for disk 26 that are below the quantification limit.

The temperature of the incubator (not shown) can be set to approximately 37.1° C. and verified prior to each test. The stainless-steel weights 22 and jar/lid 21, 28 can be allowed to equilibrate for at least 24 hours prior to use in a test. The temperature can be logged every 30 seconds to ensure temperature variance is controlled. In addition, other temperatures may be used, as required for the test program.

At least one positive control sample can be included for each test day. The purpose of the positive control is to demonstrate that the entire test process is working properly, measuring the permeated mass through a swatch 24 if breakthrough has occurred. This is accomplished by using a swatch 24 of approximately 10 mil latex rubber, which is known to have a measurable permeation mass and is used as a standard reference.

At least one negative control sample can also be included for each test day. The purpose of the negative control is to demonstrate that the entire process is working properly, and that cross-contamination from the process does not indicate breakthrough if there is none. Such cross-contamination could occur from tools or other test cells. The negative control swatches can go through the same process as the others, but no contaminant is added. A measured agent concentration indicates an issue with the process. Randomly chosen swatches of test materials can be used as negative control samples. Contaminants are not measured above the quantification limit for any of the negative control swatches Characterization samples are included for each test day. The purpose of the characterization samples is to demonstrate that for the given contaminant and material combination, measurable contaminant permeates through the test swatch 24 and does not defeat the test cell 20. The cell 20 could be defeated if contaminant wicks around the edge of the swatch 24, or if vapor quantities are sufficiently high to sorb into the sorbent detector pad 25. This could lead to an inaccurate result. Characterization samples can use an additional two-inch PTFE disk 31 (shown in FIG. 4A) between the test swatch 24 and the sorbent pad 25. For characterization samples, measurable contaminant in the sorbent pad 25 indicates that the test could be defeated for this combination of contaminant and material substrate. In addition, invalid samples may be identified with a positive response from a ring of M8 paper 33 in between the test swatch 24 and sorbent pad 25 (as shown in FIG. 4B).

The analytical methods used herein include a combination of calibration curves and quality check (QC) samples to increase confidence in the data. The quantification limit is determined by the lowest standard in the calibration curve. For example, the calibration curves can be linear, made from seven points with a range from approximately 10 to 2,394 ng/mL, with $R^2$ values ranging from approximately 0.9976 to 0.9995.

Several observations are made during this testing. This test method appears suitable for permeation testing of air impermeable materials with contaminants. The lack of signal on the negative controls indicates that cross-contamination within the test, and between test days, is sufficiently low as not to interfere with the testing. The lack of signal in the characterization samples using real swatches 24 indicates that this permeated method is a viable testing method. Characterization tests that use actual swatch samples, in addition to the PTFE barrier disks 31 between the swatch 25 and sorbent pad 24 are best at replicating the test conditions for the test swatches.

During the uptake efficiency testing, four samples are used as controls. The results from these samples demonstrate proper operation of the test method. The first control sample is a negative control. The negative control follows the same process, but the contaminant is not spiked onto the PTFE disk 26. The purpose of this control is to assess the process for cross-contamination. This sample is expected to have a result less than the quantification limit.

The second control sample is used as a positive control. The PTFE disk 26 is spiked with contaminant and the solvent is permitted to evaporate. Rather than a sorbent pad 25, the contaminated PTFE disk 26 is covered with a PTFE spacer (e.g., disk 23) and weight (e.g., weight 22). Both PTFE disks 23, 26 are extracted independently. This sample follows the same test process, but without the DVB sorbent pad 25. The purpose of this control is to benchmark the entire process for sample loss, outside of the DVB extraction. The sum of the PTFE disk 23, 26 extraction results is expected to equal the original contamination level. The difference is attributed to potential loss during the entire process.

The third control sample is used as a positive control. The PTFE disk 26 is spiked with contaminant, and the solvent is allowed to evaporate. The disk 26 is then immediately extracted. The purpose of this control is to assess the upper limit for bias and account for sample loss due to interaction with PTFE disk 26 or effects from extraction of PTFE disk 26. This sample is expected to have a result equaling the original contamination level.

The fourth control sample is used as a reverse uptake control. Rather than contaminating the PTFE disk 26, the DVB sorbent pad 25 is contaminated instead, and the solvent is permitted to sorb into the pad 25 until the sessile drop is no longer visible. The contaminated DVB sorbent pad 25 is covered with a PTFE spacer (e.g., disk 23) and the weight (e.g., weight 22) applied. The purpose of this control is to measure the transfer from the contaminated DVB pad 25 to the PTFE disk 26. This test is used to measure if there is a competing attraction by the contaminant for the PTFE disk 26 or the DVB pad 25. This sample also provides information on the extraction efficiency of the DVB pad 25; i.e., once the pad 25 sorbs a contaminant, how efficient is the extraction process. Generally, it is not possible to determine the true extraction efficiency with only one sample. The extraction efficiency has previously been measured, and this sample provides an indication of performance. The DVB pad 25 is expected to retain the contaminant during contact with the PTFE disk 26, but enables easy extraction in solvent for quantitative analysis.

In a second round of testing, permeation of 10 μg VX was measured through latex swatches tested with three different test methodologies. Using the contact method described above, the variance in the permeating measurement is reduced compared to prior test methods. It is surmised that the 1 psi pressure standardizes the contact between the test swatch 24 and sorbent pad 25, previously identified as a technical challenge in prior testing. For each of these tests, the sorbent pads 25 are extracted in solvent for approximately 30 min followed by GC-FPD analysis. A comparison of the measured permeation masses and variances is tabulated in Table 2 below. The contact method embodied herein indicates two important findings compared to prior art. First, it indicates that a greater amount of contaminant had permeated through the substrate, demonstrating that prior arts may under predict the contamination level in a contact scenario. Second, the contact results are much more reproducible as compared to prior art. This reproducibility increases confidence in the test results.

TABLE 2

Comparison of positive control samples between different test methodologies

| Method | Contact | Hybrid | Vapor |
|---|---|---|---|
| Average (μg) | 8.316 | 1.589 | 53.1 |
| % of initial deposition | 83.2% | 15.9% | 0.5% |
| Standard deviation | 512.5 | 937.2 | 12.8 |
| Standard Error | 6% | 60% | 24% |

FIG. 5, with reference to FIGS. 3A through 4B, is a flow diagram illustrating a method of testing, wherein the method comprises providing (50) a PTFE layer 26; placing (52) a sorbent pad 25 on the PTFE layer 26; applying (54) contaminants to a protective material 24; placing (56) the protective material 24 adjacent to the sorbent pad 25; applying (58) a weight 22 to the protective material 24 causing the protective material 24 to contact the sorbent pad 25, and causing the sorbent pad 25 to become exposed to the contaminants; and measuring (60) a level of contamination of the sorbent pad 25 upon exposure to the contaminated protective material 24. The method may further comprise placing a second PTFE layer 23 in between the weight 22 and the protective material 24. Additionally, another PTFE layer 31 may be placed in between the protective material 24 and the sorbent pad 25. The method may further comprise placing the PTFE layer 26 (including all of the PTFE layers 23, 26, 31), the sorbent pad 25, the protective material 24, and the weight 22 in a sealed container 21, 28 during the exposure of the sorbent pad 25 to the contaminated protective material 24. The exposure of the sorbent pad 25 to the contaminated protective material 24 may occur for approximately four hours. The protective material 24 may comprise any of air impermeable materials, air permeable materials, and semi-permeable materials.

The embodiments herein provide an enhanced expulsion test method. The lack of signal from the negative control and characterization samples indicates that this method is amenable to permeation testing in a liquid contamination-contact detection scheme. With eighty replicates, the positive control testing indicates an increase in confidence of results using this method, with a reduction in variance between samples when compared to prior testing. The lack of measured permeation mass through butyl gloves indicates that the gloves may provide suitable protection for approximately four hours from contact with contaminated surfaces or objects under real-world pressures associated with grasping or touching for the tested contaminant. Although designed for air impermeable materials, the embodiments herein may also be amenable to air permeable and semi-permeable materials for liquid-contamination-contact detection schemes.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An apparatus for measuring permeation through protective materials, comprising:
    a polytetrafluoroethylene (PTFE) layer;
    a sorbent pad on said PTFE layer;
    a protective material in contact with said sorbent pad, said protective material having contaminants applied thereon on a side opposite said sorbent pad;
    a second PTFE layer on said protective material and covering said contaminants, wherein said second PTFE layer isolates and contains said contaminants; and
    a weight applied to said second PTFE layer causing contact between said protective material and said sorbent pad in order to determine the level of permeation of said contaminants through said protective material.

2. The apparatus of claim 1, further comprising a third PTFE layer in between said protective material and said sorbent pad.

3. The apparatus of claim 1, further comprising a scaled container housing said PTFE layer, said sorbent pad, said protective material said second PTFE layer and said weight during the exposure of said sorbent pad to said contaminated protective material.

4. The apparatus of claim 1, wherein said protective material comprises any of air impermeable materials, air permeable materials, and semi-permeable materials.

5. An apparatus comprising:
a holding dish;
a first polytetrafluoroethylene (PTFE) layer placed in said holding dish;
a sorbent pad on said PTFE layer;
a protective material in contact with said sorbent pad, said protective material having contaminants applied thereon on a side opposite said sorbent pad;
a second PTFE layer on said protective material, wherein said second PTFE layer isolates and contains said contaminants;
a weight applied to said second PTFE layer causing said protective material to continuously contact said sorbent pad in order to determine the level of permeation of said contaminants through said protective material.

6. The apparatus of claim 5, further comprising a third PTFE layer in between said weight and said sorbent pad.

7. The apparatus of claim 5, father comprising a sealed container housing the first and second PTFE layers, said holding dish, said sorbent pad, said protective material, and said weight during the exposure of said sorbent pad to said contaminated protective material.

8. The apparatus of claim 5, wherein said protective material comprises any of air impermeable materials, air permeable materials, and semi-permeable materials.

9. A method of testing permeation of contaminants through protective materials, comprising:
providing a polytetrafluoroethylene (PTFE) layer;
placing a sorbent pad on said PTFB layer;
applying contaminants to a protective material;
placing said protective material adjacent to said sorbent pad;
placing a second PTFE layer on said protective material covering said contaminants, wherein said second PTFE layer isolates and contains said contaminants;
applying a weight to said second PTFE layer causing said protective material to contact said sorbent pad; and
measuring a level of contamination of said sorbent pad upon exposure to the contaminated protective material.

10. The method of claim 9, further comprising placing a third PTFE layer in between said protective material and said sorbent pad.

11. The method of claim 9, further comprising placing said PTFE layer, said sorbent pad, said protective material, said second PIPE layer, and said weight in a sealed container during the exposure at said sorbent pad to said contaminated protective material.

12. The method of claim 9, wherein said protective material comprises any of air impermeable materials, air permeable materials, and semi-permeable materials.

* * * * *